(12) United States Patent
Whitman

(10) Patent No.: US 7,114,642 B2
(45) Date of Patent: *Oct. 3, 2006

(54) EXPANDING PARALLEL JAW DEVICE FOR USE WITH AN ELECTROMECHANICAL DRIVER DEVICE

(75) Inventor: Michael P. Whitman, New Hope, PA (US)

(73) Assignee: Power Medical Interventions, Inc., Langhorne, PA (US)

( * ) Notice: Subject to any disclaimer, the term of this patent is extended or adjusted under 35 U.S.C. 154(b) by 133 days.

This patent is subject to a terminal disclaimer.

(21) Appl. No.: 10/761,492

(22) Filed: Jan. 20, 2004

(65) Prior Publication Data

US 2004/0149802 A1 Aug. 5, 2004

Related U.S. Application Data

(60) Division of application No. 10/341,234, filed on Jan. 13, 2003, now Pat. No. 6,698,643, which is a continuation of application No. 09/873,682, filed on Jun. 4, 2001, now Pat. No. 6,505,768, which is a continuation of application No. 09/351,534, filed on Jul. 12, 1999, now Pat. No. 6,264,087.

(51) Int. Cl.
*A61B 17/068* (2006.01)

(52) U.S. Cl. .................. 227/180.1; 227/19; 227/176.1; 227/178.1

(58) Field of Classification Search .................. 227/19, 227/176.1, 175.1, 180.1, 181.1, 178.1; 606/219, 606/139, 207

See application file for complete search history.

(56) References Cited

U.S. PATENT DOCUMENTS 1,798,902 A    3/1931  Raney
2,031,682 A    2/1936  Wappler et al.
2,174,219 A    9/1939  Balma
2,246,647 A    6/1941  Vancura
2,419,045 A    4/1947  Whittaker
2,725,628 A   12/1955  O'Neilly et al.
3,079,606 A    3/1963  Bobrov et al.
3,120,845 A    2/1964  Horner
3,193,165 A    7/1965  Akhalaya et al.
3,252,643 A    5/1966  Strekopytov et al.
3,253,643 A    5/1966  Gudheim
3,256,875 A    6/1966  Tsepelev et al.
3,275,211 A    9/1966  Hirsch et al.
3,315,863 A    4/1967  O'Dea
3,317,105 A    5/1967  Astafiev et al.
3,388,847 A    6/1968  Kasulin et al.

(Continued)

FOREIGN PATENT DOCUMENTS

DE          23 30 182      1/1975

(Continued)

*Primary Examiner*—Scott A. Smith
(74) *Attorney, Agent, or Firm*—Kenyon & Kenyon LLP

(57) ABSTRACT

A cutting and stapling device for use as an attachment to an electromechanical device driver comprises an upper jaw and a lower jaw which separate and close against one another in a continuously parallel alignment. The upper jaw includes a series of staple guides corresponding to one or more staples in a removable staple tray disposed within a lower jaw, whereby a blade and wedge having a threaded bore travel upon a matching threaded shaft in a channel disposed in the lower jaw below the staple tray, such that rotation of the threaded shaft causes movement of the wedge through the channel while a sloped surface of the wedge contacts the staples to push the staples against the staples guides, closing the staples.

12 Claims, 10 Drawing Sheets

U.S. PATENT DOCUMENTS

| | | |
|---|---|---|
| 3,490,576 A | 1/1970 | Alessi et al. |
| 3,490,675 A | 1/1970 | Green et al. |
| 3,494,533 A | 2/1970 | Green et al. |
| 3,499,591 A | 3/1970 | Green |
| 3,552,626 A | 1/1971 | Astafiev et al. |
| 3,589,589 A | 6/1971 | Akopov |
| 3,593,903 A | 7/1971 | Astafiev et al. |
| 3,618,842 A | 11/1971 | Bryan |
| 3,638,652 A | 2/1972 | Kelley |
| 3,643,851 A | 2/1972 | Green |
| 3,662,939 A | 5/1972 | Bryan |
| 3,675,688 A | 7/1972 | Bryan et al. |
| 3,692,224 A | 9/1972 | Astafiev et al. |
| 3,717,294 A | 2/1973 | Green |
| 3,735,762 A | 5/1973 | Bryan et al. |
| 3,777,538 A | 12/1973 | Weatherly et al. |
| 3,788,303 A | 1/1974 | Hall |
| 3,795,034 A | 3/1974 | Strekopytov et al. |
| 3,815,476 A | 6/1974 | Green et al. |
| 3,819,100 A | 6/1974 | Noiles et al. |
| 3,837,555 A | 9/1974 | Green |
| 3,844,289 A | 10/1974 | Noiles et al. |
| 3,858,577 A | 1/1975 | Bass et al. |
| 3,859,986 A | 1/1975 | Okada et al. |
| 3,882,854 A | 5/1975 | Hulka et al. |
| 3,892,228 A | 7/1975 | Mitsui |
| 3,935,981 A | 2/1976 | Akopov et al. |
| 3,949,924 A | 4/1976 | Green |
| RE28,932 E | 8/1976 | Noiles et al. |
| 4,014,492 A | 3/1977 | Rothfuss |
| 4,027,510 A | 6/1977 | Hiltebrandt |
| 4,060,089 A | 11/1977 | Noiles |
| 4,064,881 A | 12/1977 | Meredith |
| 4,085,756 A | 4/1978 | Weaver |
| 4,086,926 A | 5/1978 | Green et al. |
| 4,092,986 A | 6/1978 | Schneiderman |
| 4,111,206 A | 9/1978 | Vishnevsky et al. |
| 4,169,476 A | 10/1979 | Hiltebrandt |
| 4,198,960 A | 4/1980 | Utsugi |
| 4,198,982 A | 4/1980 | Fortner et al. |
| 4,202,479 A | 5/1980 | Razgulov et al. |
| 4,202,480 A | 5/1980 | Annett |
| 4,207,873 A | 6/1980 | Kruy |
| 4,207,898 A | 6/1980 | Becht |
| 4,244,372 A | 1/1981 | Kapitanov et al. |
| 4,250,873 A | 2/1981 | Bonnet |
| 4,261,244 A | 4/1981 | Becht et al. |
| 4,273,109 A | 6/1981 | Enderby |
| 4,273,111 A | 6/1981 | Tsukaya |
| 4,273,129 A | 6/1981 | Boebel |
| 4,289,131 A | 9/1981 | Mueller |
| 4,289,133 A | 9/1981 | Rothfuss |
| 4,296,881 A | 10/1981 | Lee |
| 4,304,236 A | 12/1981 | Conta et al. |
| 4,310,115 A | 1/1982 | Inoue |
| 4,319,576 A | 3/1982 | Rothfuss |
| 4,325,377 A | 4/1982 | Boebel |
| 4,349,028 A | 9/1982 | Green |
| 4,351,466 A | 9/1982 | Noiles |
| 4,354,628 A | 10/1982 | Green |
| 4,367,729 A | 1/1983 | Ogiu |
| 4,379,457 A | 4/1983 | Gravener et al. |
| 4,383,634 A | 5/1983 | Green |
| 4,391,401 A | 7/1983 | Moshofsky |
| 4,402,445 A | 9/1983 | Green |
| 4,429,695 A | 2/1984 | Green |
| 4,442,964 A | 4/1984 | Becht |
| 4,445,509 A | 5/1984 | Auth |
| 4,445,892 A | 5/1984 | Hussein et al. |
| 4,448,188 A | 5/1984 | Loeb |
| 4,461,305 A | 7/1984 | Cibley |
| 4,473,077 A | 9/1984 | Noiles et al. |
| 4,476,863 A | 10/1984 | Kanshin et al. |
| 4,485,817 A | 12/1984 | Swiggett |
| 4,488,523 A | 12/1984 | Schichman |
| 4,489,875 A | 12/1984 | Crawford et al. |
| 4,499,895 A | 2/1985 | Takayama |
| 4,505,272 A | 3/1985 | Utyamyshev et al. |
| 4,505,414 A | 3/1985 | Filipi |
| 4,506,670 A | 3/1985 | Crossley |
| 4,506,671 A | 3/1985 | Green |
| 4,513,746 A | 4/1985 | Aranyi et al. |
| 4,519,532 A | 5/1985 | Foslien |
| 4,520,817 A | 6/1985 | Green |
| 4,527,724 A | 7/1985 | Chow et al. |
| 4,534,352 A | 8/1985 | Korthoff |
| 4,559,928 A | 12/1985 | Takayama |
| 4,566,620 A | 1/1986 | Green et al. |
| 4,573,468 A | 3/1986 | Conta et al. |
| 4,573,622 A | 3/1986 | Green et al. |
| 4,574,806 A | 3/1986 | McCarthy |
| 4,576,167 A | 3/1986 | Noiles |
| 4,589,412 A | 5/1986 | Kensey |
| 4,589,416 A | 5/1986 | Green |
| 4,589,582 A | 5/1986 | Bilotti |
| 4,591,085 A | 5/1986 | Di Giovanni |
| 4,592,354 A | 6/1986 | Rothfuss |
| 4,593,679 A | 6/1986 | Collins |
| 4,603,693 A | 8/1986 | Conta et al. |
| 4,605,001 A | 8/1986 | Rothfuss et al. |
| 4,606,343 A | 8/1986 | Conta et al. |
| 4,607,638 A | 8/1986 | Crainich |
| 4,610,383 A | 9/1986 | Rothfuss et al. |
| 4,631,052 A | 12/1986 | Kensey |
| 4,633,861 A | 1/1987 | Chow et al. |
| 4,633,874 A | 1/1987 | Chow et al. |
| 4,643,190 A | 2/1987 | Heimberger |
| 4,646,745 A | 3/1987 | Noiles |
| 4,655,673 A | 4/1987 | Hawkes |
| 4,657,017 A | 4/1987 | Sorochenko |
| 4,664,305 A | 5/1987 | Blake, III et al. |
| 4,667,673 A | 5/1987 | Li |
| 4,669,471 A | 6/1987 | Hayashi |
| 4,671,445 A | 6/1987 | Barker et al. |
| 4,672,961 A | 6/1987 | Davies |
| 4,674,515 A | 6/1987 | Andou et al. |
| 4,688,555 A | 8/1987 | Wardle |
| 4,696,667 A | 9/1987 | Masch |
| 4,700,703 A | 10/1987 | Resnick et al. |
| 4,703,887 A | 11/1987 | Clanton et al. |
| 4,705,038 A | 11/1987 | Sjostrom et al. |
| 4,708,141 A | 11/1987 | Inoue et al. |
| 4,714,187 A | 12/1987 | Green |
| 4,715,502 A | 12/1987 | Salmon |
| 4,728,020 A | 3/1988 | Green et al. |
| 4,732,156 A | 3/1988 | Nakamura |
| 4,733,118 A | 3/1988 | Mihalko |
| 4,752,024 A | 6/1988 | Green et al. |
| 4,754,909 A | 7/1988 | Barker et al. |
| 4,756,309 A | 7/1988 | Sachse et al. |
| 4,760,840 A | 8/1988 | Fournier, Jr. et al. |
| 4,763,669 A | 8/1988 | Jaeger |
| 4,767,044 A | 8/1988 | Green |
| 4,771,774 A | 9/1988 | Simpson et al. |
| 4,776,506 A | 10/1988 | Green |
| 4,781,186 A | 11/1988 | Simpson et al. |
| 4,784,137 A | 11/1988 | Kulik et al. |
| 4,805,823 A | 2/1989 | Rothfuss |
| 4,817,847 A | 4/1989 | Redtenbacher et al. |
| 4,819,632 A | 4/1989 | Davies |
| 4,819,853 A | 4/1989 | Green |
| 4,841,888 A | 6/1989 | Mills et al. |
| 4,848,637 A | 7/1989 | Pruitt |
| 4,858,608 A | 8/1989 | McQuilkin |

| | | | | | |
|---|---|---|---|---|---|
| 4,863,088 A | 9/1989 | Redmond et al. | 5,312,023 A | 5/1994 | Green et al. |
| 4,873,977 A | 10/1989 | Avant et al. | 5,312,434 A | 5/1994 | Crainich |
| 4,887,599 A | 12/1989 | Muller | 5,318,221 A | 6/1994 | Green et al. |
| 4,887,612 A | 12/1989 | Esser et al. | 5,320,627 A | 6/1994 | Sorensen et al. |
| 4,892,244 A | 1/1990 | Fox et al. | 5,322,055 A | 6/1994 | Davison et al. |
| 4,893,622 A | 1/1990 | Green et al. | 5,324,288 A | 6/1994 | Billings et al. |
| 4,903,697 A | 2/1990 | Resnick et al. | 5,324,300 A | 6/1994 | Elias et al. |
| 4,907,591 A | 3/1990 | Vasconcellos et al. | 5,326,013 A | 7/1994 | Green et al. |
| 4,917,114 A | 4/1990 | Green et al. | 5,330,471 A | 7/1994 | Eggers |
| 4,919,152 A | 4/1990 | Ger | 5,330,486 A | 7/1994 | Wilk |
| 4,928,699 A | 5/1990 | Sasai | 5,333,773 A | 8/1994 | Main et al. |
| 4,930,494 A | 6/1990 | Takehana et al. | 5,336,229 A | 8/1994 | Noda |
| 4,932,960 A | 6/1990 | Green et al. | 5,342,381 A | 8/1994 | Tidemand |
| 4,941,623 A | 7/1990 | Pruitt | 5,350,104 A | 9/1994 | Main et al. |
| 4,944,093 A | 7/1990 | Falk | 5,352,222 A | 10/1994 | Rydell |
| 4,944,443 A | 7/1990 | Oddsen et al. | 5,352,223 A | 10/1994 | McBrayer et al. |
| 4,955,882 A | 9/1990 | Hakky | 5,352,235 A | 10/1994 | Koros et al. |
| 4,955,959 A | 9/1990 | Tompkins et al. | 5,356,408 A | 10/1994 | Rydell |
| 4,957,499 A | 9/1990 | Lipatov et al. | 5,358,506 A | 10/1994 | Green et al. |
| 4,962,877 A | 10/1990 | Hervas | 5,364,409 A | 11/1994 | Kuwabara et al. |
| 4,976,710 A | 12/1990 | Mackin | 5,366,133 A | 11/1994 | Geiste |
| 4,977,900 A | 12/1990 | Fehling et al. | 5,366,476 A | 11/1994 | Noda |
| 4,978,049 A | 12/1990 | Green | 5,383,880 A | 1/1995 | Hooven |
| 4,991,764 A | 2/1991 | Mericle | 5,391,156 A | 2/1995 | Hildwein et al. |
| 4,994,060 A | 2/1991 | Rink et al. | 5,395,033 A | 3/1995 | Byrne et al. |
| 4,995,877 A | 2/1991 | Ams et al. | 5,395,369 A | 3/1995 | McBrayer et al. |
| 5,005,749 A | 4/1991 | Aranyi | 5,396,900 A | 3/1995 | Slater et al. |
| 5,018,657 A | 5/1991 | Pedlick et al. | 5,397,046 A | 3/1995 | Savage et al. |
| 5,031,814 A | 7/1991 | Tompkins et al. | D357,535 S | 4/1995 | Grant et al. |
| 5,040,715 A | 8/1991 | Green et al. | 5,403,312 A | 4/1995 | Yates et al. |
| 5,071,430 A | 12/1991 | de Salis et al. | 5,403,326 A | 4/1995 | Harrison et al. |
| 5,104,025 A | 4/1992 | Main et al. | 5,403,327 A | 4/1995 | Thornton et al. |
| 5,108,391 A | 4/1992 | Flachenecker et al. | 5,411,508 A | 5/1995 | Bessler et al. |
| 5,119,983 A | 6/1992 | Green et al. | 5,413,267 A | 5/1995 | Solyntjes |
| 5,133,359 A | 7/1992 | Kedem | 5,425,705 A | 6/1995 | Evard et al. |
| 5,133,729 A | 7/1992 | Sjostrom | 5,425,745 A | 6/1995 | Green et al. |
| 5,137,198 A | 8/1992 | Nobis et al. | 5,433,721 A | 7/1995 | Hooven et al. |
| 5,139,513 A | 8/1992 | Segato | 5,441,507 A | 8/1995 | Wilk |
| 5,156,315 A | 10/1992 | Green | 5,456,684 A | 10/1995 | Schmidt et al. |
| 5,157,837 A | 10/1992 | Rose | 5,464,404 A | 11/1995 | Abela et al. |
| 5,158,222 A | 10/1992 | Green | 5,465,894 A | 11/1995 | Clark et al. |
| 5,170,925 A | 12/1992 | Madden et al. | 5,467,911 A | 11/1995 | Tsuruta et al. |
| 5,171,247 A | 12/1992 | Hughett et al. | 5,476,206 A | 12/1995 | Green et al. |
| 5,171,251 A | 12/1992 | Bregen et al. | 5,482,054 A | 1/1996 | Slater et al. |
| 5,173,133 A | 12/1992 | Morin et al. | 5,482,197 A | 1/1996 | Green et al. |
| 5,192,292 A | 3/1993 | Cezana et al. | 5,485,947 A | 1/1996 | Olson et al. |
| 5,197,649 A | 3/1993 | Bessler et al. | 5,496,317 A | 3/1996 | Goble et al. |
| 5,201,325 A | 4/1993 | McEwen et al. | 5,514,134 A | 5/1996 | Rydell et al. |
| 5,201,750 A | 4/1993 | Hocherl et al. | 5,518,163 A | 5/1996 | Hooven |
| 5,205,459 A | 4/1993 | Brinkerhoff et al. | 5,518,164 A | 5/1996 | Hooven |
| 5,207,691 A | 5/1993 | Nardella | 5,520,634 A | 5/1996 | Fox et al. |
| 5,207,697 A | 5/1993 | Carusillo et al. | 5,527,313 A | 6/1996 | Scott et al. |
| 5,217,460 A | 6/1993 | Knoepfler | 5,529,235 A | 6/1996 | Boiarski et al. |
| 5,249,583 A | 10/1993 | Mallaby | 5,533,661 A | 7/1996 | Main et al. |
| 5,253,793 A | 10/1993 | Green | 5,535,937 A | 7/1996 | Boiarski et al. |
| 5,254,117 A | 10/1993 | Rigby et al. | 5,562,677 A | 10/1996 | Hildwein et al. |
| 5,258,004 A | 11/1993 | Bales et al. | 5,562,702 A | 10/1996 | Huitema et al. |
| 5,258,007 A | 11/1993 | Spetzler et al. | 5,569,274 A | 10/1996 | Rapacki et al. |
| 5,258,008 A | 11/1993 | Wilk | 5,571,116 A | 11/1996 | Bolanos et al. |
| 5,261,877 A | 11/1993 | Fine et al. | 5,578,052 A | 11/1996 | Koros et al. |
| 5,267,997 A | 12/1993 | Farin et al. | 5,580,067 A | 12/1996 | Hamblin et al. |
| 5,268,622 A | 12/1993 | Philipp | 5,597,543 A | 1/1997 | Zeiringer |
| 5,271,543 A | 12/1993 | Grant et al. | 5,603,443 A | 2/1997 | Clark et al. |
| 5,271,544 A | 12/1993 | Fox et al. | 5,607,094 A | 3/1997 | Clark et al. |
| 5,275,322 A | 1/1994 | Brinkerhoff et al. | 5,618,303 A | 4/1997 | Marlow et al. |
| 5,275,609 A | 1/1994 | Pingleton et al. | 5,618,307 A | 4/1997 | Donlon et al. |
| 5,285,945 A | 2/1994 | Brinkerhoff et al. | 5,626,607 A | 5/1997 | Malecki et al. |
| 5,289,963 A | 3/1994 | McGarry et al. | 5,653,374 A | 8/1997 | Young et al. |
| 5,290,299 A | 3/1994 | Fain et al. | 5,665,100 A | 9/1997 | Yoon |
| 5,290,303 A | 3/1994 | Pingleton et al. | 5,667,517 A | 9/1997 | Hooven |
| 5,292,053 A | 3/1994 | Bilotti et al. | 5,667,526 A | 9/1997 | Levin |
| 5,295,990 A | 3/1994 | Levin | 5,676,674 A | 10/1997 | Bolanos et al. |
| 5,300,087 A | 4/1994 | Knoepfler | 5,688,269 A | 11/1997 | Newton et al. |

| | | | | | | |
|---|---|---|---|---|---|---|
| 5,697,543 A * | 12/1997 | Burdorff ............... 227/176.1 | EP | 0 216 532 | 4/1987 |
| 5,732,871 A | 3/1998 | Clark et al. | EP | 0 293 123 | 11/1988 |
| 5,735,848 A | 4/1998 | Yates et al. | EP | 0 324 166 | 7/1989 |
| 5,735,849 A | 4/1998 | Baden et al. | EP | 0 324 637 | 7/1989 |
| 5,735,861 A | 4/1998 | Peifer et al. | EP | 0 365 153 | 4/1990 |
| 5,741,285 A | 4/1998 | McBrayer et al. | EP | 0 369 324 | 5/1990 |
| 5,749,893 A | 5/1998 | Vidal et al. | EP | 0 373 762 | 6/1990 |
| 5,779,130 A | 7/1998 | Alesi et al. | EP | 0 399 701 | 11/1990 |
| 5,779,132 A | 7/1998 | Knodel et al. | EP | 0 484 677 | 5/1992 |
| 5,782,396 A | 7/1998 | Mastri et al. | EP | 0 514 139 | 11/1992 |
| 5,782,397 A | 7/1998 | Koukline | EP | 0 536 903 | 4/1993 |
| 5,823,956 A | 10/1998 | Roth et al. | EP | 0 539 762 | 5/1993 |
| 5,855,590 A | 1/1999 | Malecki et al. | EP | 0 552 050 | 7/1993 |
| 5,868,760 A | 2/1999 | McGuckin, Jr. | EP | 0 598 579 | 5/1994 |
| 5,893,875 A | 4/1999 | O'Connor et al. | EP | 0 621 006 | 10/1994 |
| 5,897,562 A | 4/1999 | Bolanos et al. | EP | 0 627 006 | 10/1994 |
| 5,913,842 A | 6/1999 | Boyd et al. | EP | 0 630 612 | 12/1994 |
| 5,954,259 A | 9/1999 | Viola et al. | EP | 0 639 349 | 2/1995 |
| 6,004,335 A | 12/1999 | Vaitekunas et al. | EP | 0 679 367 | 11/1995 |
| 6,110,188 A | 8/2000 | Narciso, Jr. | EP | 0 552 423 | 1/1998 |
| 6,119,913 A | 9/2000 | Adams et al. | EP | 0 581 400 | 5/2000 |
| 6,126,058 A | 10/2000 | Adams et al. | GB | 1 352 554 | 5/1974 |
| 6,193,129 B1 | 2/2001 | Bittner et al. | GB | 1 452 185 | 10/1976 |
| 6,264,087 B1 * | 7/2001 | Whitman ............... 227/180.1 | GB | 2 044 108 | 10/1980 |
| 6,368,340 B1 | 4/2002 | Malecki et al. | GB | 2 048 685 | 12/1980 |
| 6,505,768 B1 * | 1/2003 | Whitman ............... 227/180.1 | GB | 2 165 559 | 4/1986 |
| 6,698,643 B1 * | 3/2004 | Whitman ............... 227/180.1 | GB | 2180455 | 4/1987 |
| 2001/0016750 A1 | 8/2001 | Malecki et al. | NL | 7711347 | 4/1979 |
| 2001/0031975 A1 | 10/2001 | Whitman et al. | SU | 659146 | 4/1979 |
| | | | WO | WO 83/00992 | 3/1983 |
| | | | WO | WO 90/05491 | 5/1990 |
| | | | WO | WO 90/06085 | 6/1990 |
| | | | WO | WO 92/16141 | 10/1992 |
| | | | WO | WO 93/08754 | 5/1993 |
| | | | WO | WO95/18572 | 7/1995 |

FOREIGN PATENT DOCUMENTS

| | | |
|---|---|---|
| DE | 31 14 135 | 10/1982 |
| DE | 4213426 | 10/1992 |
| EP | 0 593 920 | 4/1974 |
| EP | 0 041 022 | 12/1981 |
| EP | 0 116 220 | 8/1984 |
| EP | 0 156 774 | 10/1985 |

* cited by examiner

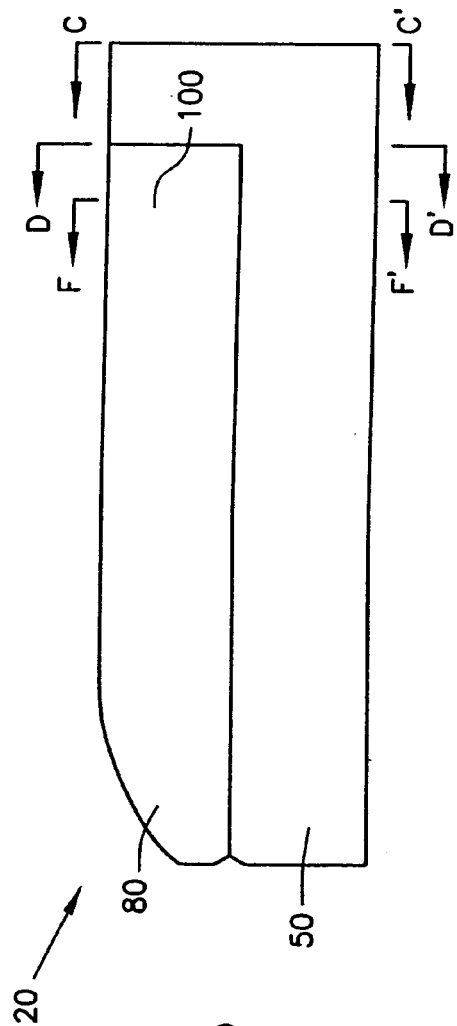
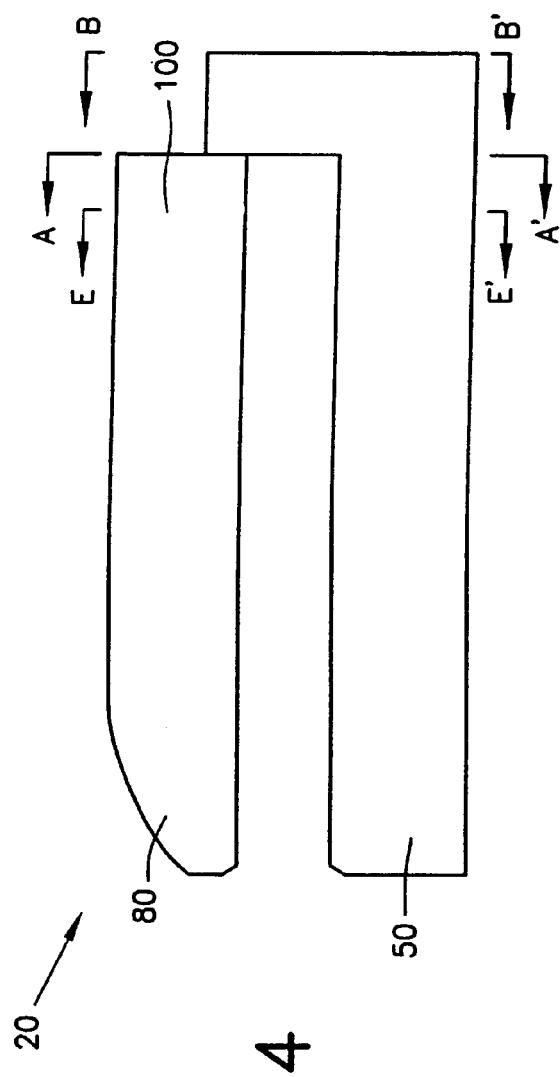
Fig. 3
Fig. 4

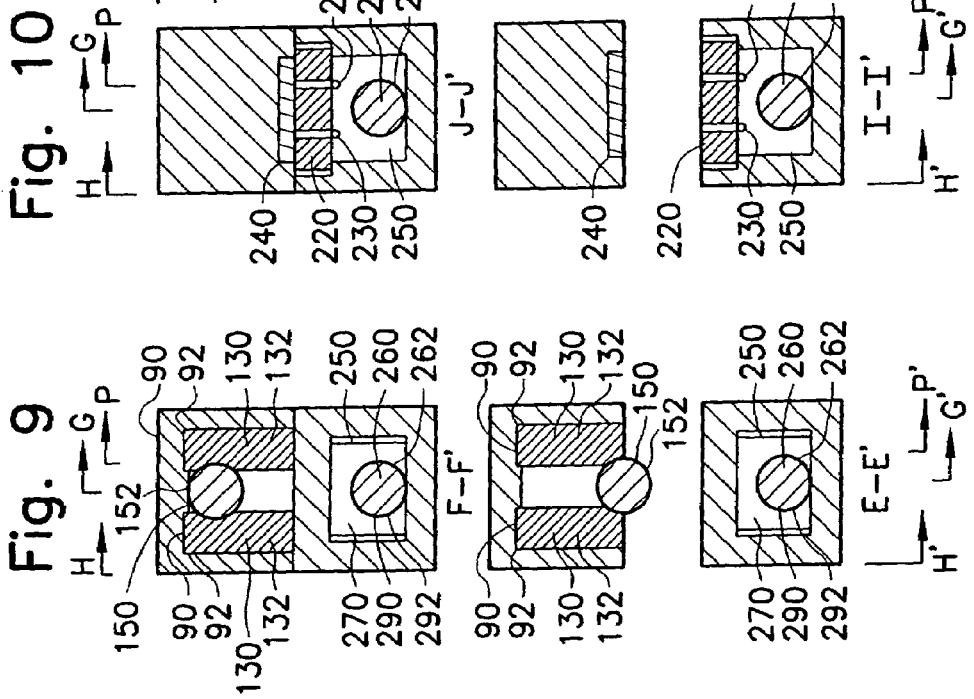
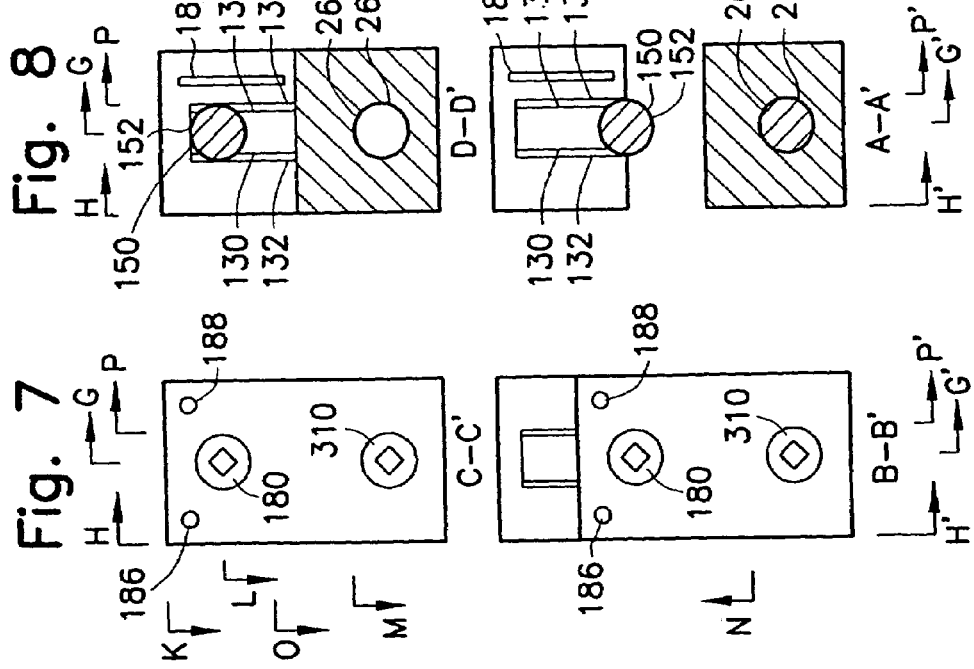

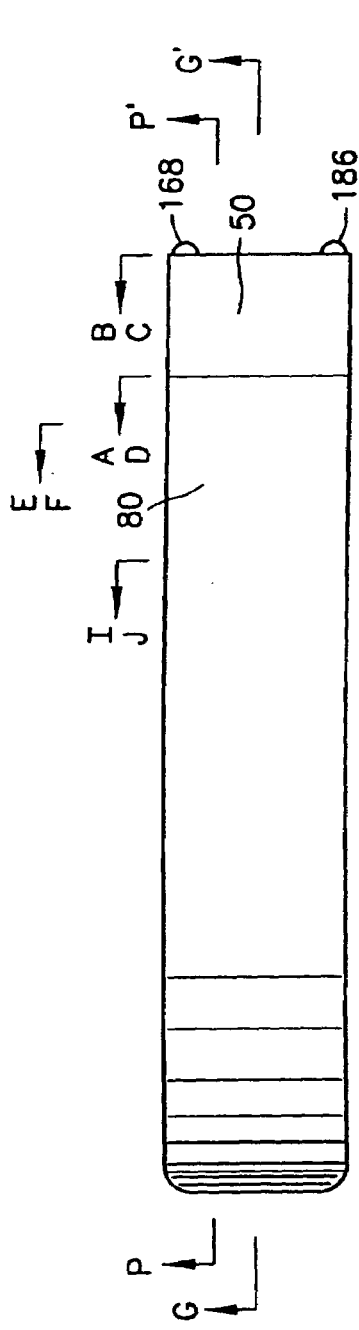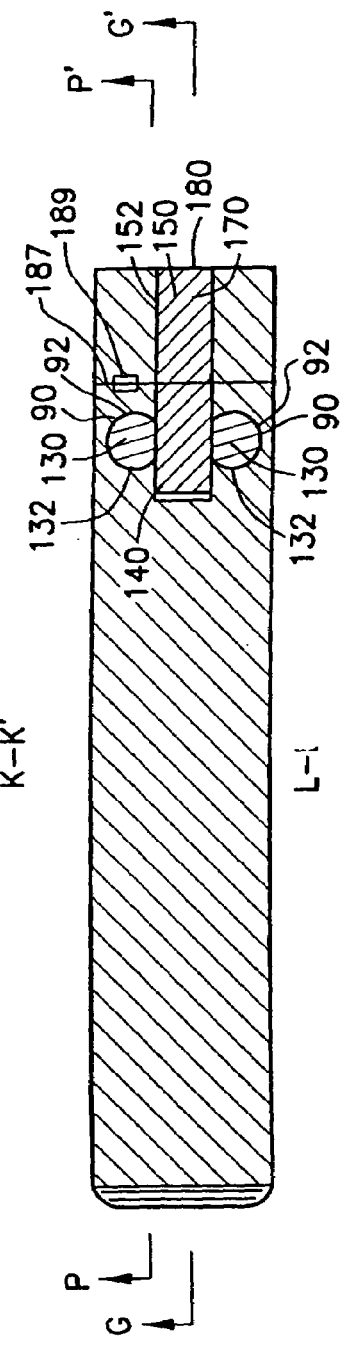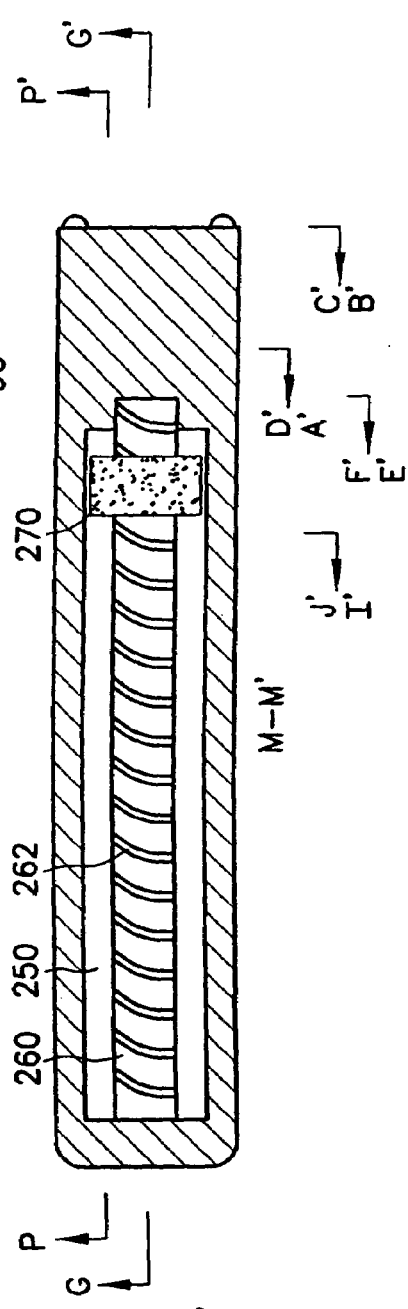

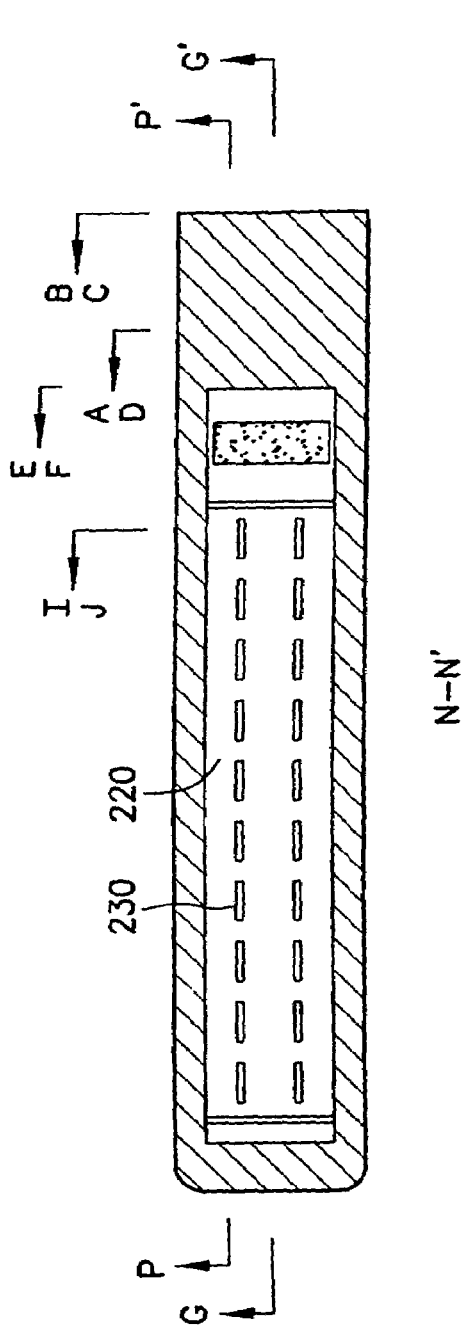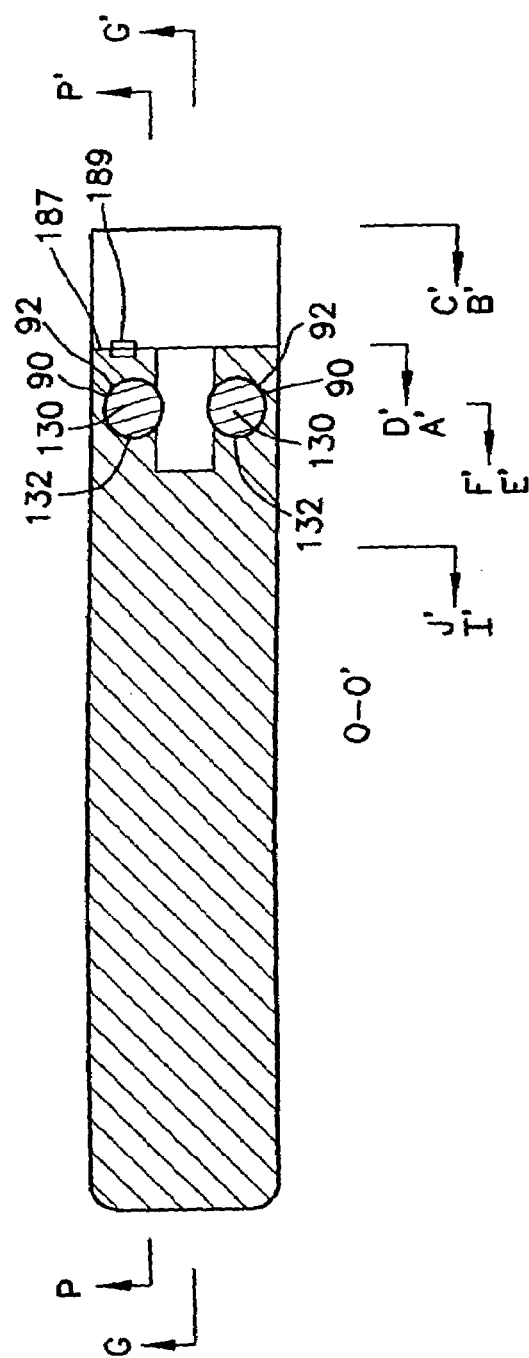
Fig. 18
Fig. 19

EXPANDING PARALLEL JAW DEVICE FOR USE WITH AN ELECTROMECHANICAL DRIVER DEVICE

CROSS-REFERENCE TO RELATED APPLICATIONS

This application is a division of U.S. application Ser. No. 10/341,234, filed on Jan. 13, 2003, which is now U.S. Pat. No. 6,698,643, which is a continuation of U.S. application Ser. No. 09/873,682, filed on Jun. 4, 2001, now U.S. Pat. No. 6,505,768, which is a continuation of U.S. application Ser. No. 09/351,534, which was filed on Jul. 12, 1999, now U.S. Pat. No. 6,264,087, each of which is expressly incorporated herein in its entirety by reference thereto.

BACKGROUND OF THE INVENTION

1. Field of the Invention

The present invention relates generally to an attachment for an electromechanical device for use with anastomosing, stapling, and resecting surgical tools, and more specifically to a stapling and resecting device which can be attached to and serve as an extension of an electromechanical device driver, and most specifically to the expanding parallel jaws and the mechanisms thereof.

2. Description of the Prior Art

Upon identification of cancerous and other anomalous tissue in the gastrointestinal tract, surgical intervention is often prescribed. The field of cancer surgery, and more specifically, the surgical procedure by which a section of the gastrointestinal tract which includes cancerous tissue is resected, includes a number of uniquely designed instruments. In combination with a description of the present instrumentation and their functions, a description of the state of the art in this surgical procedure shall also be provided.

The first question which must be answered when determining how to treat gastrointestinal tract cancer relates to the specific location of the cancerous tissue. This is very important insofar as the instruments which are provided in the present art have limitations relating to how far they may be inserted into the gastrointestinal tract. If the cancerous tissue is too far up or down the gastrointestinal tract, then the standard instrumentation provided is unusable, thus requiring special accommodations. These accommodations generally increase the risk of contamination of the surrounding tissues with bowel contents, increase the length of the surgery and the corresponding need for anesthesia, and eliminate the benefits of precise anastomosing and stapling which comes from utilizing a mechanized device.

More specifically, in the event that the cancerous tissue is located at a position in the colon which is accessible by the present instrumentation, the patient's abdomen is initially opened to expose the bowel. The surgeon then cuts the tube of the colon on either side of the cancerous tissue, while simultaneously stapling closed the two open ends of the bowel (a distal end which is directed toward the anus, and the proximal end which is closest to the lower intestine). This temporary closure is performed in order to minimize contamination. The linear cutter and stapling instrument which is used in the prior art is provided in a perspective view in FIG. 1.

More particularly, this temporary closure is achieved when the colon is placed between the scissoring elements at the tip of the linear cutter and stapling instrument. By squeezing the trigger in the handle of the device, the surgeon causes the scissoring elements to come together. A second trigger (or a secondary action of the same trigger) is then actuated to drive a series of staples and a cutting blade through the clamped end of the colon, thereby closing and transecting the ends.

After the sealing of the two exposed distal and proximal ends, the surgeon creates a small opening in the proximal end of the bowel and inserts the removable anvil portion of an anastomosing and stapling instrument. This step, as well as those of the remainder of the surgical procedure, are related to the functioning of this surgical instrument which is provided in a perspective view in FIG. 2. More particularly, the surgeon begins by taking the instrument and manually turning the dial at the base of the handle which causes the anvil head at the opposite end to advance forward. The surgeon continues to turn the dial until the anvil head advances to its most extreme extended position. This manual turning requires nearly thirty full rotations. Once fully extended, the anvil head of the instrument is decoupled therefrom and is inserted into the exposed proximal end such that the coupling post extends outwardly therethrough. As described above, this proximal end is then stapled closed. The extending shaft of the anastomosing, and stapling instrument is then inserted and advanced into the lower colon, transanally, until the coupling stem thereof extends through the stapled distal end. The surgeon then joins the coupling ends of the anvil and shaft together and begins to manually rotate the dial in the handle again, this time bringing the anvil head closer to the tip of the shaft.

Once the anvil head and shaft are brought close together, after the surgeon has manually rotated the dial another thirty times, a grip-style trigger in the handle is manually actuated. This actuation causes a circular blade to advance axially out from the tip of the shaft, and into contact with the opposing face of the anvil. The blade cuts through the stapled-closed ends of the proximal and distal ends of the colon, thereby also cutting a new pair of ends of the proximal and distal portions of the colon. The tissue which has been severed is held in an interior volume at the end of the shaft.

In lock step with the cutting, the freshly opened ends are joined together by a series of staples which are advanced through holes in the perimeter of the tip of the shaft (being pressed against and closed by the opposing face of the anvil). The coupled shaft and anvil are then withdrawn from the patient More particularly with respect to the structural features of the linear stapling instrument of the prior art which is provided in FIG. 1, the device comprises a pistol grip-styled structure having an elongate shaft and distal portion. The distal portion includes a pair of scissors-styled gripping elements which clamp the open ends of the colon closed. In fact only one of the two scissors-styled gripping elements, the anvil portion, moves (pivots) relative to overall structure; the other remains fixed. The actuation of this scissoring means (the pivoting of the anvil portion) is controlled by means of a grip trigger maintained in the handle. A number of different means have been disclosed for holding the tips of the scissoring arms closed, including snaps, clips, collars, et al.

In addition to the scissoring means, the distal portion also includes a stapling mechanism. The non-moving element of the scissoring mechanism includes a staple cartridge receiving region and a mechanism for driving the staples up through the clamped end of the colon, against the anvil portion, thereby sealing the previously opened end. The scissoring elements may be integrally formed with the shaft, or may be detachable such that various scissoring and stapling elements may be interchangeable.

More particularly with respect to the structural features of the anastomosing and stapling instrument of the prior art which is provided in FIG. 2, the device comprises an anvil portion, a staple, blade and reservoir portion, a shaft portion, and a handle portion. The anvil portion, which is selectively removable from the tip of the shaft, is bullet shaped, having a blunt nosed top portion, a flat cutting support surface on the bottom, and a coupling post extending axially from the bottom surface.

The staple, blade, and reservoir portion (SBR portion) of the instrument is provided at the distal end of the instrument, and includes a selectively advanceable and retractable coupling stem for selectively receiving thereon the anvil portion. This action of the coupling stem is provided by a screw threaded shaft and worming mechanism mounted in the handle (described more fully below). The SBR portion is cylindrical in shape, forming a housing which has a hollow interior. It is this hollow interior which forms the reservoir. The blade is similarly cylindrical, and seats in the inside of the housing, against the inner wall thereof. The blade is selectively advanceable axially outward from the housing, in accordance with actuation of a trigger mechanism of the handle (again, described more fully below). On the axially outward facing surface of the cylindrical wall of the housing are a series of staple ports, through which the staples of the device are discharged. The same actuation which drives the blade forward similarly lives a series of staple drivers forward within the cylindrical walls. More accurately, the staple driver is a cylindrical component which has a series of protuberances on the axial end thereof, the protuberances being positioned in accordance with the distribution of staples and holes. The staples, prior to being discharged, are mounted in the holes; and they are advanced through the holes by the action of the staple driver and the protuberances thereof.

The shaft portion of the instrument is a simple rigid extended structure which is intended as a sheath for a pair of elongate rods. The first rod is coupled to the worming mechanism introduced above, and described more fully below with respect to the handle portion, and is the means by which the anvil portion and the coupling stem of the SBR portion are selectively advanced and retracted. The second rod is coupled to the trigger of the handle at one end (also introduced above, and described more fully below) and to the blade and staple driver at the other end. The sheath protects the patient and the, instrument when it is advanced into the colon transanally. The nature of the actuation mechanisms however, requires that the shaft be rigid. This rigidity limits the length of the shaft; and combination, i.e. the length and rigidity of the instrument, these features limit the sections of the colon which may be treated using this device.

The handle of this instrument of the prior art comprises a pistol grip styled structure having a turning dial at the butt (i.e. the end opposing the junction of the shaft portion which the handle) and a finger actuated trigger. The trigger includes a safety mechanism which physically prevents actuation unless moved out of the interference position. The turning dial is actionable coupled to a worming mechanism which is used to advance the first rod of the shaft portion (thereby advancing the coupling stem and the anvil). The trigger functions as a basic lever to push the second rod forward within the shaft, thereby advancing the blade and staple driver.

As with many such devices of the prior art, all of these devices are considered fully disposable, and are, in fact, thrown away after a single use. They are complicated devices, having multiple moving parts, requiring substantial structural integrity and, therefore, expense in manufacturing. The fact that they are used only once, and no part can be used again render the use of such devices expensive and wasteful of resources.

In addition to this failure, as can be readily observed from the preceding descriptions, the prior art devices suffer from numerous other limitations which would be desirable to overcome. These include the rigid and limited length shaft of the devices, as well as the requirement that the surgeon manually actuate all of the features and functions.

Therefore, it is a principal object of the present invention to provide an instrument for resecting and stapling gastrointestinal tissue during colon surgery, which reduces the waste of resources by permitting use as an attachment to an electromechanical device driver.

It is further an object of the present invention to provide an instrument assembly which reduces the requirements for the surgeon to manually actuate different components and mechanisms.

It is further an object of the present invention to provide a resecting and stapling mechanism that can be integrated with other electromechanical devices into an attachment for use with an electromechanical device driver.

Other objects of the present invention shall be recognized in accordance with the description thereof provided hereinbelow, and in the Detailed Description of the Preferred Embodiment in conjunction with the remaining Figures.

SUMMARY OF THE INVENTION

The preceding objects of the invention are provided by virtue of an electromechanical resecting and stapling attachment which is coupleable to and remotely actuateable by an electromechanical device driver. In particular, the attachment includes a pair of linearly spreading jaws for clamping the selected section of gastrointestinal tissue therebetween, said jaws expanding and closing in a parallel disposition. More particularly, the linear clamping mechanism of the attachment is used to first clamp the section of colon, and then to hold the colon in place as a blade extends along a track in the lower jaw of the clamping attachment to cut the section of bowel, and then drives a series of staples through the two opened ends so that the contents of the bowel are not permitted to empty into the surrounding region of the abdomen. This attachment, and others necessary to perform the remainder of the surgery, is coupled to an electromechanical driver which is described more fully hereinbelow.

More particularly, with respect to the electromechanical driver, the driver has a handle and a flexible drive shaft. The handle has a pistol grip-styled design, having a pair of finger triggers which are independently coupled to separate motors which each turn separate flexible drive shafts (described more fully, hereinbelow). The motors are each dual direction motors, and are coupled to a manual drive switch mounted to the top of the handle, by which the user can selectively alter the turning direction of each motor. This dual direction capacity may be most simply achieved by selecting motors which turn in a direction corresponding to the direction of current, and actuation of the drive switches alters the direction of the current accordingly. In this example, the power source supplying the motors must be a direct current source, such as a battery pack (and most desirably, a rechargeable battery pack). In the event that the device should be useable with an alternating current, either a transformer can be included, or a more sophisticated intermediate gearing assembly may be provided. In conjunction with the present description, the embodiments of the present invention which will be described utilize a rechargeable battery pack providing a direct current In addition to the motor components, the handle further includes several other features, including: (1) a remote status indicator; (2) a shaft steering means; and (3) at least one additional electrical supply. First, the remote status indicator may comprise an LCD (or similar read out device) by which the user may gain knowledge of the position of components (for example whether a clamping element is in the proper position prior to the driving of the staples). Second, the handle also includes a manually actuateable steering means, for example, a joystick or track ball, for directing the movement of the flexible shaft (by means of guidewaves implanted in the shaft portion described more fully hereinbelow). Finally, the handle may include an additional electrical power supply and an on off switch for selectively supplying electrical power to the attachments.

More particularly, with respect to the flexible shaft, the shaft comprises a tubular sheath, preferably formed of a simple elastomeric material which is tissue compatible and which is sterilizable (i.e. is sufficiently rugged to withstand an autoclave). Various lengths of this shaft may be provided in conjunction with the present invention. In this case, the flexible shaft and the handle portions should be separable. If separable, the interface between the proximal end of the shaft and the distal end of the handle should include a coupling means for the drive components. Specifically regarding the drive components of the shaft, within the elastomeric sheath are a pair of smaller fixed tubes which each contain a flexible drive shaft which is capable of rotating within the tube. The flexible drive shaft, itself, simply must be capable of translating a torque from the motor in the handle to the distal end of the shaft, while still being flexible enough to be bent, angled, curved, etc. as the surgeon deems necessary to "snake" through the bowel of the patient. For example, the drive shafts may comprise a woven steel fiber cable. It shall be recognized that other drive shafts may be suitable for this purpose. In order for the distal end of the drive shaft to couple with an attachment, such as the clamping and stapling device of the present invention (as described more fully below), however, the distal tips of the drive shafts must have a conformation which permits the continued translation of torque. For example, the distal tips of the drive shafts may be hexagonal, thereby fitting into a hexagonal recess in the coupling interface of the attachment. As suggested above, in conjunction with the manually actuateable steering means mounted to the handle, the sheath further includes at least two guidewires which are flexible, but are coupled to the inner surface of the sheath near the distal end thereof The guidewires may be axially translated relative to one another by actuation of the steering means, which action causes the sheath to bend and curve accordingly. Also, as suggested above, in conjunction with tie LCD indicator of the handle, the shaft further contains an electrical lead for coupling to the attachments. This electrical lead channels a signal from the attachment to the handle for indicating the status of the attachment (for example, whether a clamping function is holding). Similarly, a second electrical lead may be provided to supply power to separate aspects of the attachment if so required (for example, as will be described more fully with respect to linear resecting and stapling attachment, the use of selectively engageable electromagnetic seal for ensuring continued clamping through the stapling process may be provided and require power selectively provided from the handle's power supply).

More particularly, with respect to the linear resecting, clamping, and stapling attachment which is the specific subject of this invention, the attachment is fitted with two drive extensions, which in operation function as extensions of the flexible drive shafts of the electromechanical driver. That is, when the attachment is mated to the electromechanical driver, the drive extensions are in mechanical communication with the flexible drive shafts such that the activation of the drive shaft motors activates the drive extensions within the linear clamping, cutting and stapling attachment The first drive extension enables the parallel spreading and closing of the jaws of the device, which form a linear clamping mechanism, while the second drive extension enables a cutting and stapling mechanism. More particularly, the linear clamping mechanism comprises a separating jaw system whereby an upper jaw is raised to permit the bowel tissue to be placed therebetween, and subsequently the jaws are closed to meet to effect a clamping. In a first embodiment, the first drive extension engages a pair of threaded vertical shafts which raise or lower the upper jaw depending on the turning direction of the corresponding motor in the electromechanical driver. In a second embodiment, the first drive extension includes only a single angled gearing mechanism mounted at the end of the horizontally rotating shaft (which is coupled to one of the turning shafts of the electromagnetic driver). This gearing mechanism causes the vertically rotation of a threaded shaft on which the upper jaw is separately mounted. In both embodiments, when the jaws are closed, a pair of sensor electrodes disposed on the jaws come into contact and thereby complete a sensor circuit which alerts the surgeon that it is safe or appropriate to activate the resecting and stapling mechanism and/or automatically activates the resecting and stapling mechanism.

In each of these embodiments, the second driver causes a blade to slide along a track in the lower jaw, which blade cuts the bowel, briefly leaving two open ends. Nearly simultaneous with the cutting, a stapling mechanism drives a series of staples upwardly through opening in the lower jaw, toward the upper jaw, through the open ends, thereby closing the bowel segments. This stapling action happens nearly simultaneous with the cutting in part because the blade is contiguous with a stapling mechanism of the present invention.

This stapling mechanism begins with a replaceable tray of open staples which is set within the lower jaw, the tray having two rows of staples separated along the long axis of the jaw so that the blade may track between the rows. The opposing upper jaw face includes a set of corresponding staple guides, such that when the linear clamping mechanism is in a closed position, the open staples immediately oppose the corresponding staple guides. This mechanism comprises a wedge pushing system whereby once the linear clamping mechanism is in a closed position, the blade and a wedge ride along together in a channel below the tray of open staples, and the staples are pushed up toward the staple guides, through the bowel. More particularly, as the wedge moves through the channel a sloping surface of the wedge pushes the open staples against the corresponding staple guides, thereby closing the staples. After the staples have been closed, the wedge is pulled back through the channel. It is the first drive mechanism which lifts the jaws apart in parallel; and it is the second drive mechanism which pushes or pulls the wedge and blade mechanism through the channel. The direction of the first and second mechanisms is related solely to the remote operation of the driver, and the corresponding turning direction of the shafts, of the electromechanical driver.

BRIEF DESCRIPTION OF THE DRAWINGS

FIGS. 3 and 4 are side views of the closed and open dispositions, respectively, of a linear clamping, cutting and stapling attachment which is an aspect of the present invention;

FIGS. 7–14 are rear views in various cutaway planes of the linear clamping, cutting and stapling attachment shown in FIGS. 3–6 which is an aspect of the present invention;

FIGS. 15–19 are bottom, top cutaway, deep top cutaway, bottom cutaway, and top views, respectively, of the linear clamping cutting and stapling attachment shown in FIGS. 3–14 which is an aspect of the present invention;

DETAILED DESCRIPTION OF THE PREFERRED EMBODIMENTS

Figure 1:
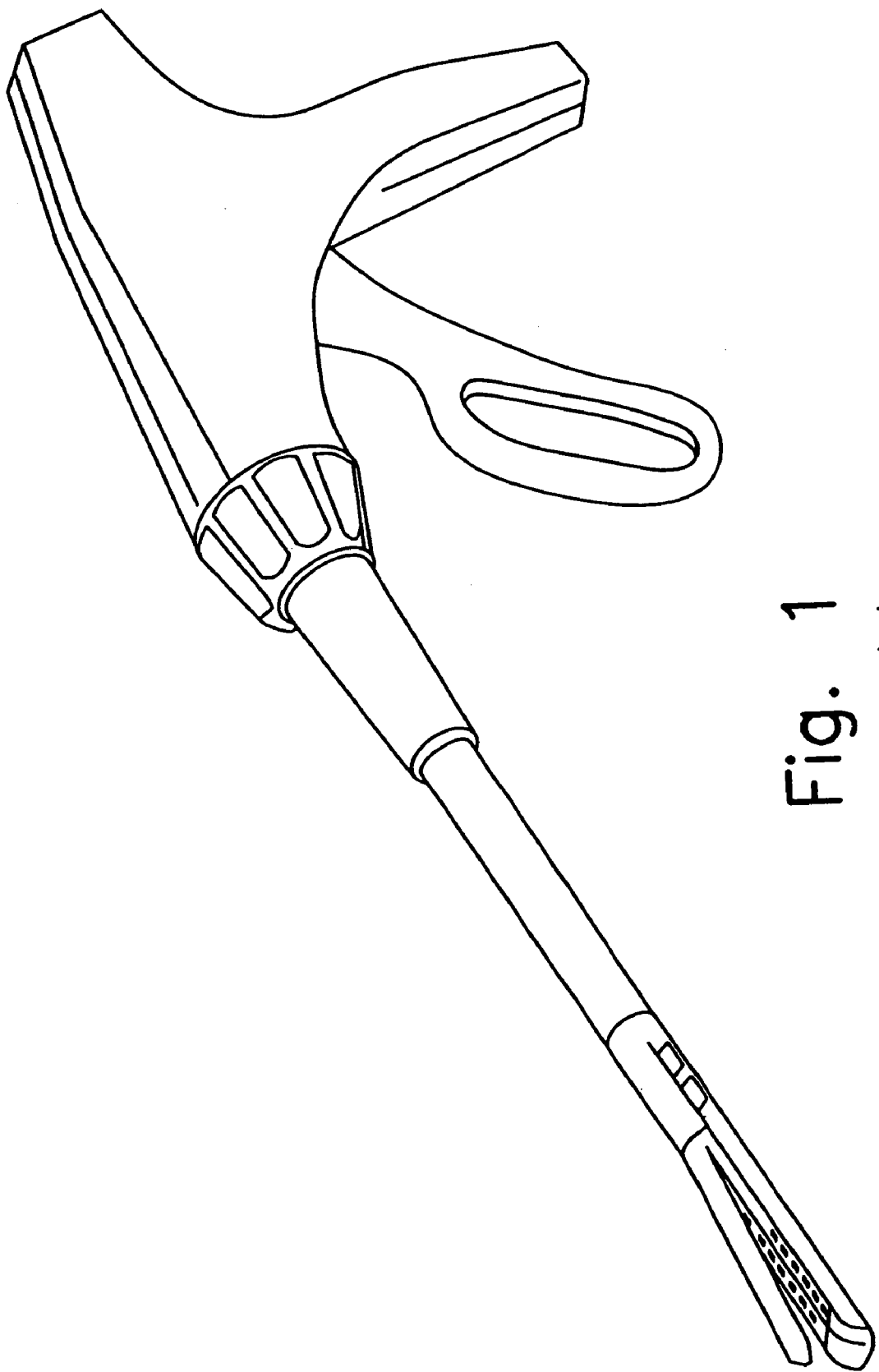
FIG. 1 is a perspective view of a linear clamping, cutting and stapling mechanism of the prior art.
Figure 2:
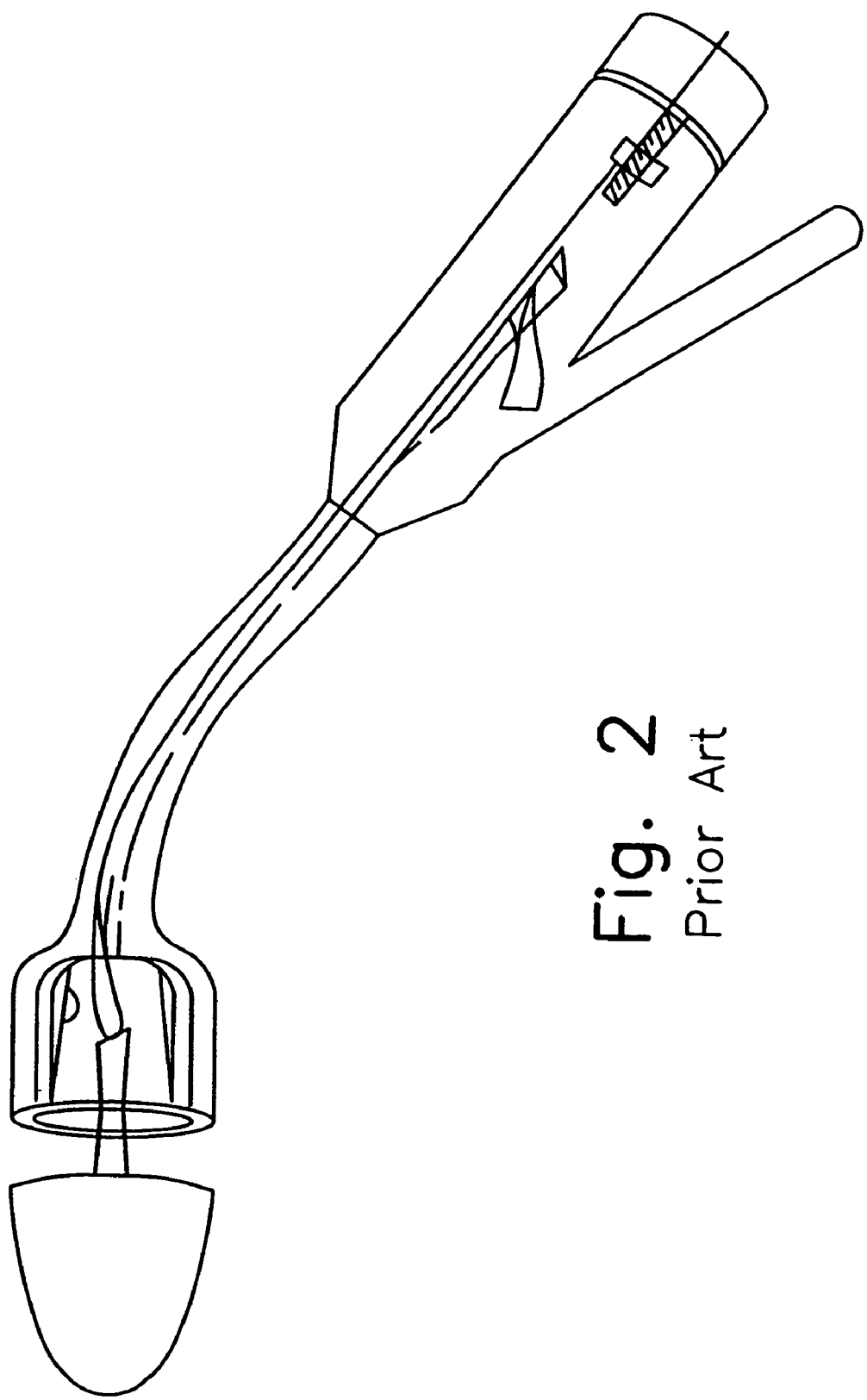
FIG. 2 is a perspective view of an anastomosing and stapling mechanism of the prior art.
Figure 5:
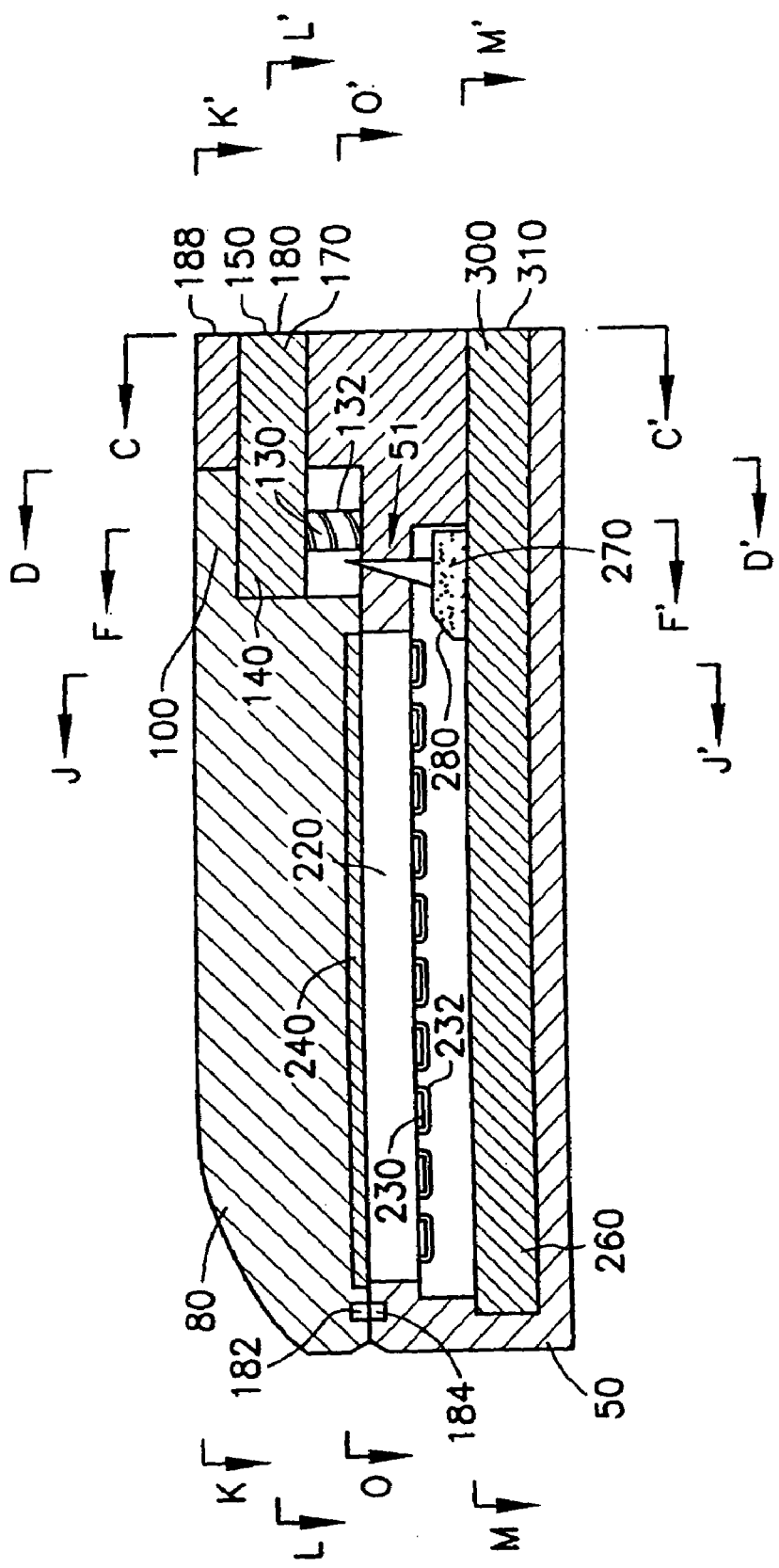
FIGS. 5 and 6 are cutaway side views of the closed and open dispositions, respectively, of the linear clamping, cutting and stapling attachment shown in FIGS. 3–4 which is an aspect of the present invention.
Figure 5A:
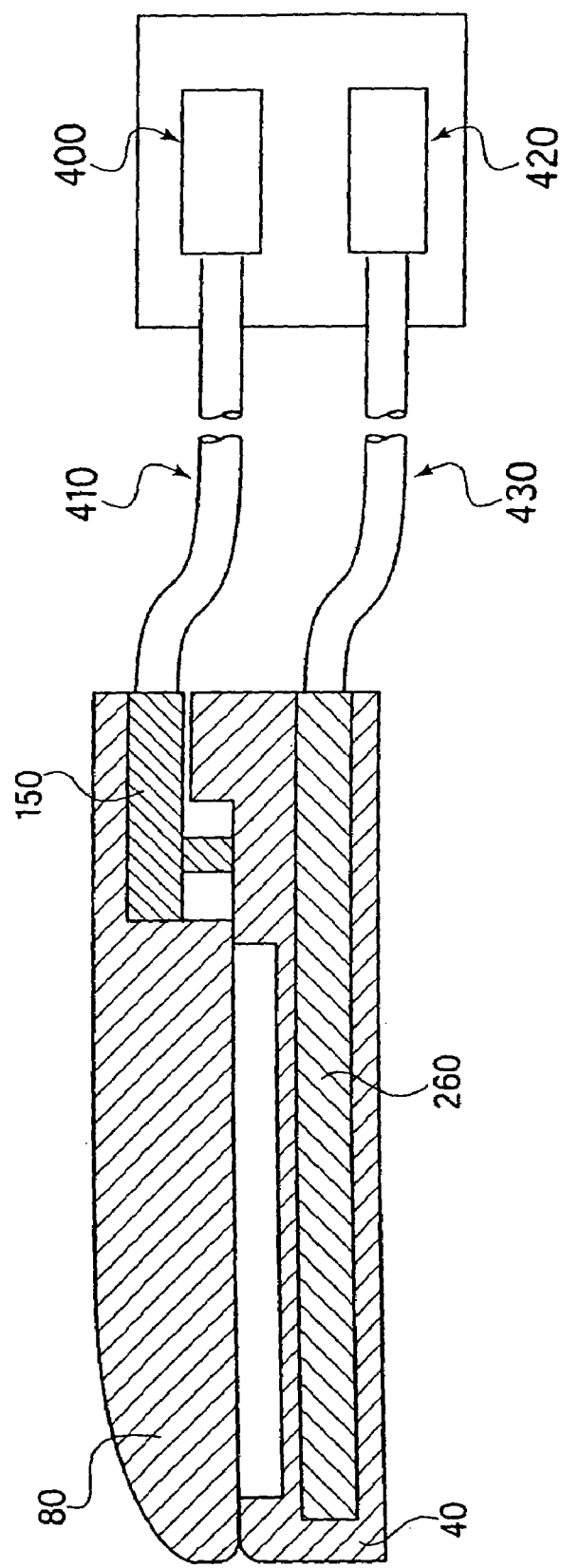
FIG. 5A is another cutaway view of the closed disposition of the linear clamping, cutting and stapling attachment shown in FIGS. 3–6, which is an aspect of the present invention.
Figure 6:
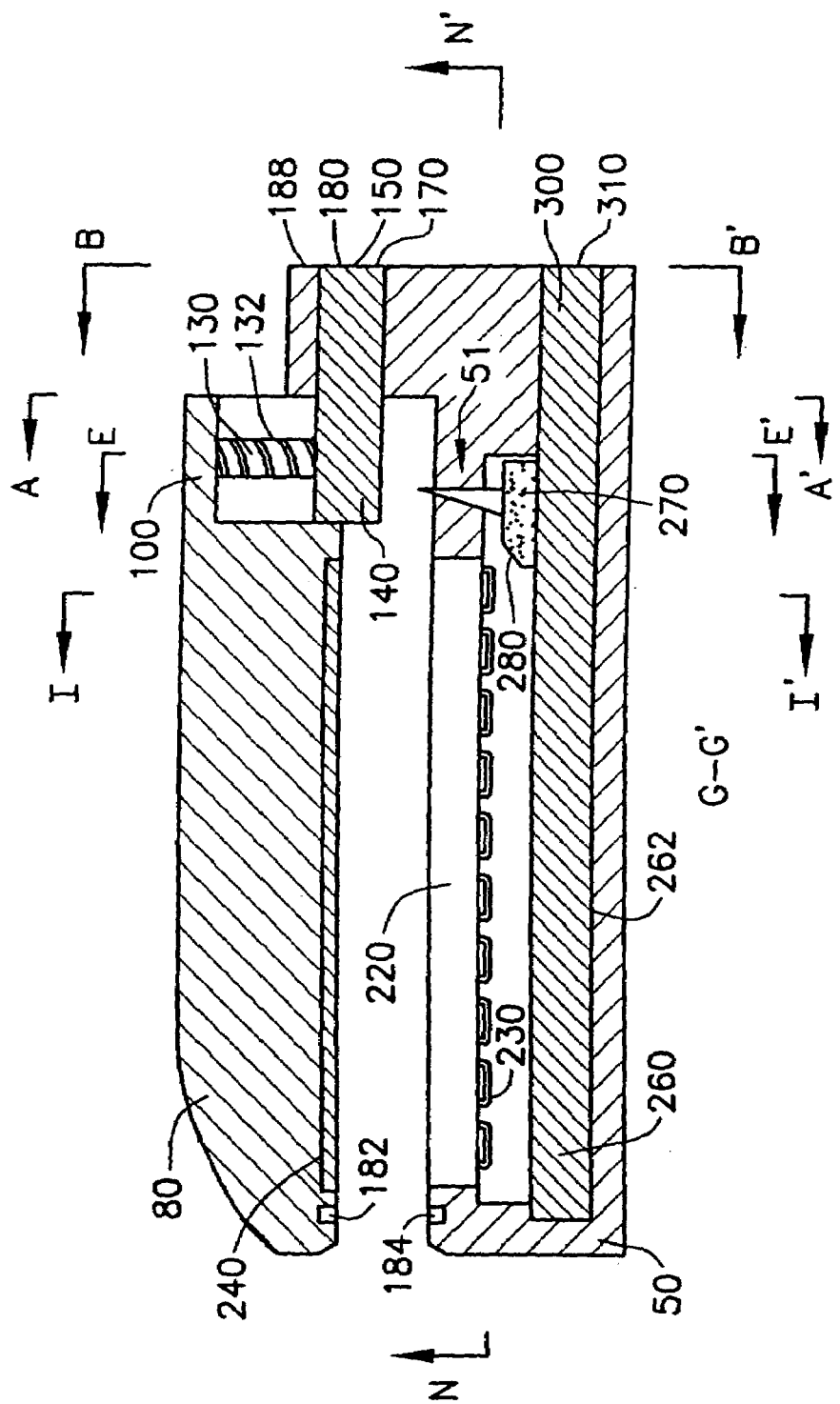
Figure 20:
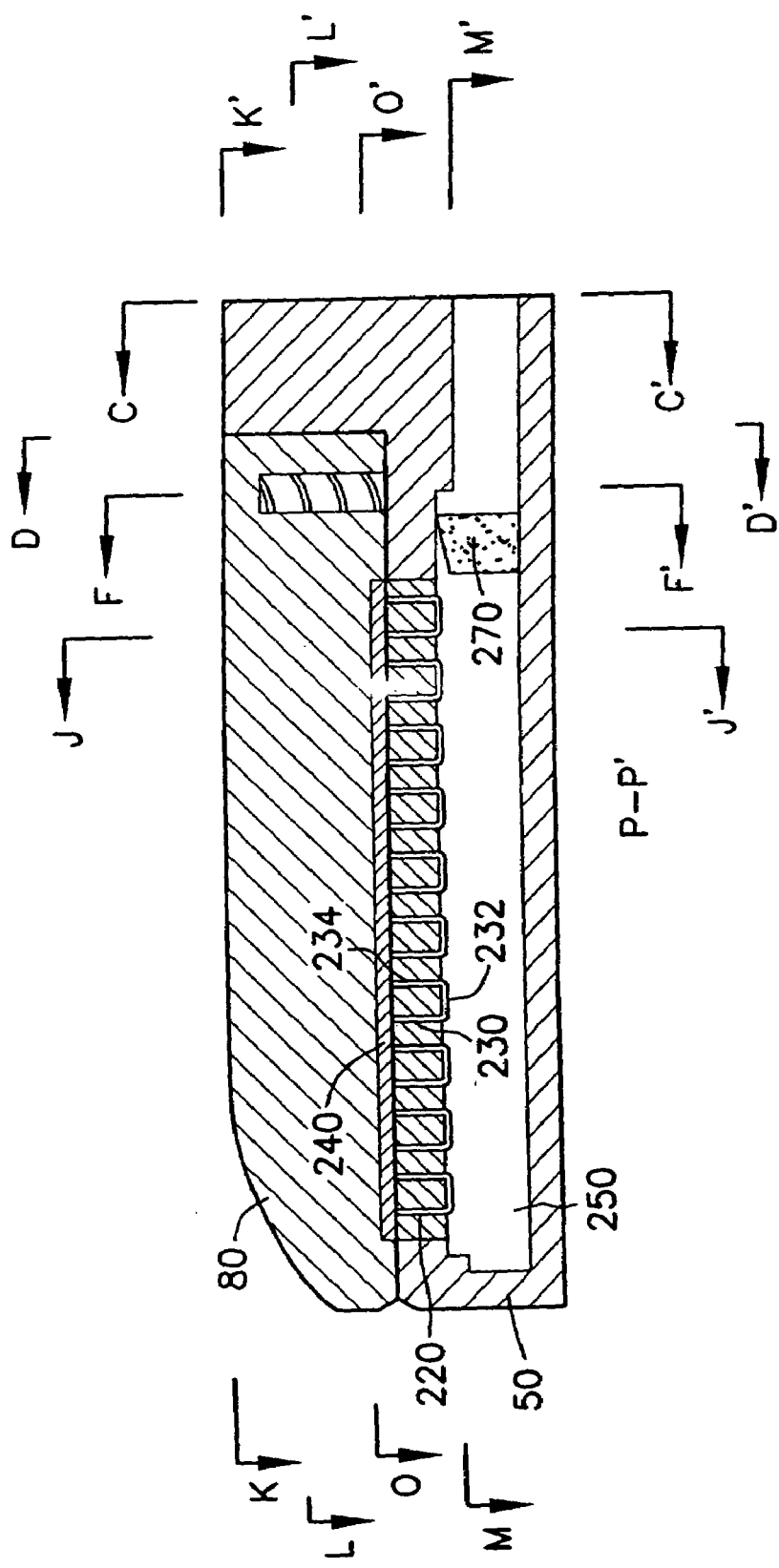
FIG. 20 is a side cutaway of the linear clamping, cutting and stapling attachment shown in FIGS. 3–19 which is an aspect of the present invention.

A preferred embodiment of the resecting and stapling attachment having expanding jaws which remain parallel according to the present invention, is illustrated in FIGS. 3–20. More particularly, referring now to FIGS. 3, 4 and 15, a linear clamping mechanism and a stapling and cutting mechanism according to the present invention are shown as part of a linear clamping, cutting and stapling attachment 20. Referring now also to FIGS. 5 and 6, in this preferred embodiment, the linear clamping mechanism comprises a parallel separating jaw system comprising a lower jaw 50 and an upper jaw 80 having a proximal end 100. Referring now also to FIGS. 9, 13, 16 and 19, the proximal end 100 of the upper jaw 80 has a pair of threaded vertical bores 90, through which extend a corresponding pair of vertical shafts 130. Inner threads 92 of the vertical bores 90 match outer threads 132 of the vertical shafts 130. Referring now also to FIGS. 8 and 12, the vertical shafts 130 engage a threaded upper horizontal shaft 150 at a distal end 140 of the upper horizontal shaft 150. Outer threads 152 of the upper horizontal shaft 150 interlock with the outer threads 132 of the vertical shafts 130. Referring now to FIGS. 5–7 and 11, the upper horizontal shaft 150 has at a proximal end 170 an upper drive socket 180.

Referring to FIGS. 5–8, 11, 12, 16 and 19, the linear clamping and cutting mechanism further comprises a first sensor electrode 182 electrically communicating via communication wires (not shown) with a first contact pad 187 (best shown in FIGS. 8, 12, 16 and 19) which in turn electrically communicates with a second contact pad 189 (best shown in FIGS. 14 and 17) via direct contact, which electrically communicates via communication wires (not shown) with a first contact node 188 (best shown in FIGS. 7, 11 and 15). Similarly, the linear clamping mechanism further comprises a second sensor electrode 184 electrically communicating via communication wires (not shown) with a second contact node 186 (best shown in FIGS. 7, 11 and 15). The contact nodes 186,188 electrically communicate with communication wires (not shown) in the electro mechanical drive component (not shown) to form a sensor circuit, such that when the upper jaw 80 and the lower jaw 50 are clamped together, the sensor electrodes 182, 184 are in contact, the sensor circuit is closed, and the surgeon is alerted via other circuit components (not shown) to the clamped position of the jaws 50, 80, and is therefore informed that it is safe and/or appropriate to active the stapling mechanism.

Further in this preferred embodiment, and referring now to FIGS. 5, 6, 10, 14, 18 and 20, the cutting and stapling mechanism comprises a wedge pushing system comprising in the lower jaw 50 a replaceable tray 220 housing one or more fastening rods, or staples 230, and in the upper jaw 80 one or more staple guides 240 corresponding to the staples 230. Each of the staples 230 has a butt 232 protruding below the tray 220, and a pair of prongs 234 extending to the top of the tray 220. Referring now also to FIGS. 9, 13 and 17, the wedge pushing system further comprises a wedge guide, or channel 250 extending beneath the tray 220. Within the channel 250 extends a threaded lower horizontal shaft 260 having outer threads 262. Upon the lower horizontal shaft 260 travels a wedge 270 having a sloped top face 280, a horizontal threaded bore 290 (best shown in FIGS. 9 and 12) coaxial with the channel 250, having and inner threads 292 matching the outer threads 262 of the lower horizontal threaded shaft 260, and an upwardly extending blade member 51. Referring now to FIGS. 5, 6, 7 and 11, the lower horizontal shaft 260 has at a proximal end 300 a second drive socket 310.

In operation, after the surgeon has located the cancerous or anomalous tissue in the gastrointestinal tract, the patient's abdomen is initially opened to expose the bowel. Utilizing the remote actuation provided by the electromechanical driver assembly, the surgeon drives the upper and lower jaws of the linear cutting and stapling attachment into the open position. The surgeon then places the tube of the bowel on a side adjacent to the cancerous tissue between the parallel spread jaws. Again, by remote actuation, the surgeon causes the upper drive mechanism to engage in reverse, and the upper jaw closes, in a parallel alignment, onto the bowel and the lower jaw. Once the bowel has been sufficiently clamped, the surgeon engages the second drive mechanism, which causes the blade and wedge staple driver to advance simultaneously, thereby cutting and stapling the bowel. The surgeon then repeats this step on the other side of the cancerous tissue, thereby removing the section of bowel containing the cancerous tissue, which is stapled on either end to prevent spilling of bowel material into the open abdomen.

More particularly, the linear clamping, cutting and stapling attachment is mated to the attachment socket (not shown) of the electromechanical driver component (not shown) such that the upper drive socket 180 engages the corresponding flexible drive shaft (not shown) of the electromechanical driver component (not shown) and the second drive socket 310 engages the corresponding flexible drive shaft (not shown) of the electromechanical driver component (not shown). Thus, rotation of the upper horizontal shaft 150 is effected by rotation of the upper drive socket 180 which is effected by rotation of the corresponding flexible drive shaft (not shown) of the electromechanical driver component (not shown). Clockwise or counter-clockwise rotation is achieved depending on the direction of the responsible motor (not shown). Similarly, rotation of the lower horizontal shaft 260 is effected by rotation of the second drive socket 310 which is effected by rotation of the corresponding flexible drive shaft (not shown) of the electromechanical driver component (not shown). Again, clockwise or counter-clockwise rotation is achieved depending on the direction of the responsible motor (not shown).

In order to clamp the exposed ends of the bowel, the surgeon first activates the upper motor 400 corresponding to the upper flexible drive shaft 410 which engages the upper drive socket 180 at the proximal end 170 of the upper horizontal shaft 150, thereby causing the upper horizontal shaft 150 to turn in a clockwise rotation. When the linear clamping and stapling attachment is in an initial closed state as shown in FIG. 3, this clockwise rotation of the upper horizontal shaft 150 causes the outer threads 152 of the upper horizontal shaft 150 to engage the outer threads 132 of the vertical shafts 130, thereby closing the vertical shafts 130 to turn in a clockwise rotation. This clockwise rotation of the vertical shafts 130 causes the outer threads 132 of the vertical shafts 130 to channel within the inner threads 92 of the vertical bores 90, thereby causing the upper jaw 80 to rise in a continuous fashion, in a parallel alignment with the fixed lower jaw, and begin separating from the lower jaw 50. Continuous operation of the motor in this manner eventually places the linear clamping and stapling attachment in an, open state, providing a space between the upper jaw 80 and the lower jaw 50, as shown in FIG. 4. Once the linear clamping and stapling attachment is in this open state, the surgeon has access to the tray 220 of staples 230, and can check to ensure that the staples 230 are ready for the procedure and/or replace the tray 220 with a more suitable tray 220. Once the surgeon has verified that the tray 220 is ready and in place, the surgeon places the open distal end of the colon between the upper jaw 80 and lower jaw 50. Thereafter, the surgeon reverses the upper motor 400 to effect a counter-clockwise rotation of the upper horizontal shaft 150, which in turn effects counter-clockwise rotation of the vertical shafts 130, which in turn effects a lowering of the upper jaw 80, also in continuous parallel alignment. Continuous operation of the upper motor 400 in this manner eventually returns the linear clamping and stapling attachment to a closed state, where the distal end of the bowel is clamped between the upper jaw 80 and the lower jaw 40, with a small portion of the distal end of the bowel extending laterally beyond the upper jaw 80 and the lower jaw 50.

Once the distal end of the bowel is clamped as described above, the sensor electrodes 182,184 are in contact, and the surgeon is alerted via circuit components in the electromechanical drive component that it is safe and/or appropriate to activate the cutting and stapling mechanism. The surgeon then activates the cutting and stapling mechanism It should be noted that the resistance afforded by the mechanical relationships between the upper jaw 80, vertical bores 90, vertical shafts 130, horizontal shaft 150, and upper drive socket 180 of the linear clamping and stapling attachment, and the upper flexible drive shaft and upper motor 400 of the electromechanical driver component, together ensure that the upper jaw 80 and lower jaw 50 remain clamped together during the operation of the stapling mechanism. To begin the stapling and cutting procedure, the surgeon activates the lower motor 420 of the electromechanical driver component corresponding to the lower flexible drive shaft 430 which engages the lower drive socket 310 at the proximal end 300 of the lower horizontal shaft 260, thereby causing the lower horizontal shaft 260 to turn in a clockwise rotation. When the stapling and cutting mechanism is in an initial loaded state, the wedge 270 and the blade 51 associated therewith are in the channel 250 at a position closest to the proximal end 300 of the lower horizontal shaft 260. The clockwise rotation of the lower horizontal shaft 260 causes the outer threads 262 of the lower horizontal shaft 260 to engage the inner threads 292 of the horizontal threaded bore 290 of the wedge 270, thereby causing the wedge 270 to travel through the channel 250 in a direction away from the proximal end 300 of the lower horizontal shaft 260. Continuous operation of the lower motor 420 in this manner will move the wedge 270 fully through the channel 250. As the wedge 270 moves through the channel the blade 51 mounted to the top of the wedge cuts through the bowel, transecting it. Simultaneously, the sloped top face 280 of the wedge 270 contacts the butts 232 of the staples 230, thereby pushing the prongs 234 of the staples 230 through the tissue of the clamped distal end of bowel and against the staple guides 240, which bends-and closes the staples 230. When the wedge 270 is moved fully through the channel 250, all of the staples 230 are pushed through the tray 220 and closed, thereby stapling closed the distal end of the bowel. Thereafter, the surgeon reverses the lower motor 420 to effect a counter-clockwise rotation of the lower horizontal shaft 260, which in turn moves the wedge 270 toward the proximal end 300 of the lower horizontal shaft 260. Continuous operation of the lower motor 420 in this manner eventually returns the wedge 270 to its initial position.

Thereafter, the surgeon again activates the upper motor 400 to effect a clockwise rotation of the upper horizontal shaft 150, which in turn effects a clockwise rotation of the vertical shafts 130, which in turn effects a raising of the upper jaw 80. Continuous operation of the upper motor 400 in this manner eventually places the linear clamping, cutting and stapling attachment into an open state. Thereafter, the surgeon replaces the empty tray 220 with a full tray 220, and performs the same clamping, cutting and stapling procedure on the proximal end of the bowel. Once the proximal end of the bowel is also clamped, cut and stapled, the surgeon may separate the attachment from the electromechanical driver component, discard the attachment, and use the electromechanical driver component for additional procedures with other attachments.

What is claimed is:

1. A fastening and cutting attachment for use with an electromechanical driver device for cutting and fastening a section of tissue, comprising:
    a first jaw having a longitudinal axis;
    a second jaw disposed in parallel and opposed correspondence with the first jaw;
    a first rotatable shaft rotatable about a longitudinal axis arranged in parallel to the longitudinal axis of the first jaw, the first rotatable shaft coupled to the first jaw and adapted to cause the first jaw to travel linearly in a direction perpendicular to the longitudinal axes while maintaining the parallel correspondence between the first and second jaws; and
    a tray of fasteners disposed in one of the first jaw and the second jaw.

2. The fastening and cutting attachment according to claim 1, wherein the tray is selectively removable from the one of the first jaw and the second jaw.

3. The fastening and cutting attachment according to claim 1, wherein the tray is selectively replaceable.

4. A fastening and cutting device for cutting and fastening a section of tissue, comprising:
    a first jaw having a longitudinal axis;
    a second jaw disposed in parallel and opposed correspondence with the first jaw;

a first rotatable shaft rotatable about a longitudinal axis arranged in parallel to the longitudinal axis of the first jaw, the first rotatable shaft coupled to the first jaw and adapted to cause the first jaw to travel linearly in a direction perpendicular to the longitudinal axes while maintaining the parallel correspondence between the first and second jaws;

a cutter and stapler disposed within the second jaw and adapted to cut and fasten the section of tissue disposed between the first and second jaws when the first and second jaws are in a closed position;

a second rotatable shaft rotatable about a longitudinal axis arranged in parallel to the longitudinal axis of the first jaw and the longitudinal axis of the first rotatable shaft, the second rotatable shaft adapted to cause the cutter and stapler to travel linearly in a direction parallel to the longitudinal axes; and a tray of fasteners disposed in one of the first jaw and the second jaw.

5. The fastening and cutting device according to claim 4, wherein the tray is selectively removable from the one of the first jaw and the second jaw.

6. The fastening and cutting device according to claim 4, wherein the tray is selectively replaceable.

7. A fastening and cutting device for cutting and fastening a section of tissue, comprising:

a first jaw;

a second jaw disposed in parallel and opposed correspondence with the first jaw;

a first driver coupled to the first jaw, the first driver including a first horizontal rotatable shaft adapted to cause the first jaw to linearly travel along an axis perpendicular to the parallel correspondence of the first and second jaws, the first horizontal rotatable shaft being rotatable about a longitudinal axis arranged in parallel to the parallel correspondence of the first and second jaws, the first jaw separating from the second jaw when the first horizontal rotatable shaft is rotated in a first direction to open the jaws, the first jaw closing toward the second jaw when the first horizontal rotatable shaft is rotated in a second direction opposite to the first direction to close the jaws;

a cutter and linear stapler device disposed in one of the first jaw and the second jaw, the cutter and linear stapler device coupled to a second driver, the cutter and linear stapler device being adapted to cut and staple a section of tissue disposed between the first and second jaws once the first jaw has been closed toward the second jaw, the cutter and linear stapler device including a tray of staples disposed in one of the first jaw and the second jaw.

8. The fastening and cutting device according to claim 7, wherein the tray is selectively removable from the one of the first jaw and the second jaw.

9. The fastening and cutting device according to claim 7, wherein the tray is selectively replaceable.

10. A fastening and cutting attachment for use with an electromechanical driver device for cutting and fastening a section of tissue, comprising:

a first jaw;

a second jaw disposed in parallel and opposed correspondence with the first jaw;

a first driver coupled to the first jaw, the first driver being actionably coupleable to the electromechanical driver device, the first driver including a first horizontal rotatable shaft adapted to cause the first jaw to linearly travel along an axis perpendicular to the parallel correspondence of the first and second jaws, the first horizontal rotatable shaft being rotatable about a longitudinal axis arranged in parallel to the parallel correspondence of the first and second jaws, the first jaw separating from the second jaw when the first horizontal rotatable shaft is rotated in a first direction to open the jaws, the first jaw closing toward the second jaw when the first horizontal rotatable shaft is rotated in a second direction opposite to the first direction to close the jaws; and a tray of fasteners disposed in one of the first jaw and the second jaw.

11. The fastening and cutting device according to claim 10, wherein the tray is selectively removable from the one of the first jaw and the second jaw.

12. The fastening and cutting device according to claim 10, wherein the tray is selectively replaceable.

* * * * *